United States Patent [19]

Shetty et al.

[11] Patent Number: 5,198,308
[45] Date of Patent: Mar. 30, 1993

[54] TITANIUM POROUS SURFACE BONDED TO A COBALT-BASED ALLOY SUBSTRATE IN AN ORTHOPAEDIC IMPLANT DEVICE

[75] Inventors: H. Ravindranath Shetty, Warsaw; Mark A. Heldreth, Mentone; Jack E. Parr, North Webster, all of Ind.

[73] Assignee: Zimmer, Inc., Warsaw, Ind.

[21] Appl. No.: 633,597

[22] Filed: Dec. 21, 1990

[51] Int. Cl.$^5$ ............... A61F 2/28; A61F 2/30; B32B 15/14
[52] U.S. Cl. ................... 428/608; 428/660; 428/668; 623/16
[58] Field of Search ............ 428/608, 605, 613, 660, 428/668; 623/16

[56] References Cited

U.S. PATENT DOCUMENTS

| | | | |
|---|---|---|---|
| 2,847,302 | 8/1958 | Long | 428/660 |
| 2,906,008 | 9/1959 | Boegehold et al. | 428/660 |
| 3,605,123 | 9/1971 | Hahn | 3/1 |
| 3,820,167 | 6/1974 | Sivash | 3/1 |
| 3,906,550 | 9/1975 | Rostoker et al. | 3/1.912 |
| 3,943,576 | 3/1976 | Sivash | 3/1 |
| 4,530,884 | 7/1985 | Erickson et al. | 428/608 |
| 4,595,637 | 6/1986 | Eaton | 428/608 |
| 4,636,219 | 1/1987 | Pratt et al. | 623/22 |
| 4,650,109 | 3/1987 | Crivella et al. | 228/194 |
| 4,813,965 | 3/1989 | Roberts | 623/66 |
| 4,842,517 | 6/1989 | Kawahara et al. | 623/16 |
| 4,855,101 | 8/1989 | Mohs et al. | 419/8 |
| 4,889,685 | 12/1989 | Shimamune et al. | 623/16 |
| 4,969,907 | 11/1990 | Koch et al. | 623/20 |
| 4,976,738 | 12/1990 | Frey et al. | 623/16 |
| 5,080,679 | 1/1992 | Pratt et al. | 623/23 |

FOREIGN PATENT DOCUMENTS

| | | | |
|---|---|---|---|
| 330606 | 8/1989 | European Pat. Off. | 623/16 |
| 2142554A | 1/1985 | United Kingdom | 623/16 |
| 2142544B | 3/1987 | United Kingdom . | |

OTHER PUBLICATIONS

"Specifications of Zimmer Implant Metals", Dec. 1961, 623/16, 1 page.
Biomet Inc.-AGC Total Knee System-Aug. 1989.
Zimmer, Inc.-Current Topics In Orthopaedic Technology-vol. 2, No. 3-"Use of Dissimilar Metals in Orthopaedic Implants"-Lit. No. 97-2000-85 1989.
"Corrosion of Orthopaedic Implants"-Scales et al.-JBJS, vol. 41B, No. 4, Nov. 1959-pp. 810-820.
"Past Experience in the Use of Dissimilar Metals in Orthopaedic Surgery"-Materials and Orthopaedic Surgery-Mears, 1979 pp. 123-124.
"The Use of Dissimilar Metals in Surgery," Mears-J. Biomed. Mater. Res. Symposium, No. 6, pp. 133-148 1975.
The Sivash Total Hip Prosthesis-U.S. Surgical Corporation No date available.

Primary Examiner—John Zimmerman
Attorney, Agent, or Firm—Margaret L. Geringer

[57] ABSTRACT

A femoral component of a knee prosthesis, including a cobalt-based alloy substrate and a titanium fiber metal pad bonded thereto by means of an interlayer of a cobalt-based alloy including nickel. More specifically, a method of bonding a titanium porous surface to a cobalt-based alloy in an orthopaedic implant device, by first applying an interlayer of a cobalt-based alloy including nickel to the substrate and then bonding a porous structure to the interlayer. In one embodiment, an interlayer of L-605 is first applied to a substrate of Co-Cr-Mo by diffusion bonding at approximately 2200° F. and then a fiber metal pad of CP-titanium is diffusion bonded to the interlayer at approximately 1650° F. A layer of CP-titanium may optionally be placed intermediate the fiber metal pad and interlayer before the second diffusion step. In an alternative embodiment, MP-35N alloy may be substituted for the L-605 alloy.

10 Claims, 1 Drawing Sheet

TITANIUM POROUS SURFACE BONDED TO A COBALT-BASED ALLOY SUBSTRATE IN AN ORTHOPAEDIC IMPLANT DEVICE

BACKGROUND OF THE INVENTION

The present invention relates generally to orthopaedic implant devices of the type having a porous surface into which bone tissue can grow or surgical cement can enter and, more particularly, to a method of bonding a porous surface structure of titanium or a titanium alloy onto a substrate of a cobalt-based alloy, whereby enhanced bonding strength and corrosion resistance is achieved.

Orthopaedic implant devices commonly include a porous surface to enhance attachment of the device to adjacent bone tissue. Consequently, various methods have developed for manufacturing an implant device having a porous surface. One such method involves securing a porous fiber metal structure, i.e., a wire mesh pad, to a portion of the surface of the device where bone ingrowth or attachment is desired. While the fiber metal pad generally provides a suitable porous surface, efforts to develop improved methods of attaching the pad to the implant surface continue. For instance, it is a desired to further improve the bonding strength and corrosion resistance of the attachment interface.

In several orthopaedic implant applications, it is desired to combine dissimilar metals in order to take advantage of the particular strength, biocompatibility, and corrosion resistance properties of the respective metals. For instance, as disclosed in UK Patent GB 2142544 B to Medcraft, it is known to combine a cobalt-based alloy with titanium or a titanium alloy, wherein one constitutes the substrate of an implant device and the other constitutes a wire mesh that is diffusion bonded to the substrate to provide a porous surface. However, diffusion bonding of commercially pure titanium porous structure (such as a porous pad) onto cobalt-based alloys requires elevated temperatures which reduces corrosion resistance of the composite structure. Furthermore, diffusion bonding of titanium porous structure directly onto a cobalt-based alloy does not produce necessary bond strength in the structure.

In another application involving a cobalt-based alloy and titanium, the femoral component of a knee prosthesis is fabricated by casting a cobalt-based alloy substrate and then securing a titanium fiber metal pad to the surface of the substrate by first plasma spraying a titanium coating on the surface. This bonding method is disclosed in U.S. Pat. No. 4,969,907 to Koch et al.

Both of the aforementioned bonding arrangements result in the formation of an alloy at the interface between components that tends to exhibit some corrosion at the interfacing layers. Nevertheless, it desired to provide an improved method of bonding a titanium porous surface to the surface of a cobalt-based alloy substrate, wherein bonding strength and corrosion resistance are enhanced.

SUMMARY OF THE INVENTION

The present invention provides an orthopaedic implant device having a porous surface, wherein a titanium porous structure is bonded to the surface of a cobalt-based alloy substrate by an interlayer comprising a cobalt-based alloy including nickel. Such interlayer may also include additional elements, such as tungsten. Generally, the nickel, or nickel and tungsten, contained in the bonding interlayer tends to form an alloy with the titanium porous structure at their bonding interface that enhances the corrosion resistance properties of the resulting assembly.

More specifically, the bonding process of the present invention involves first applying the bonding interlayer to the substrate, and then bonding the porous structure to the interlayer. In this manner, a dual cycle process is established whereby a lower process temperature can be used for the titanium bonding step, thereby minimizing unwanted corrosion problems.

An advantage of the orthopaedic implant device of the present invention is that a titanium porous surface is provided on a cobalt-based alloy substrate with enhanced bonding strength and corrosion resistance properties.

An advantage of the bonding method of the present invention is that a titanium porous structure can be bonded to a cobalt-based alloy substrate.

Another advantage of the bonding method of the present invention is that a dual cycle bonding process is employed whereby different bonding temperatures can be used, thereby protecting the metallurgical properties of the component alloys and determining bonding strengths at the respective interfaces between alloys.

The invention, in one form thereof, provides an orthopaedic implant device having enhanced corrosion resistance properties. The device includes a substrate of a cobalt-based alloy, and a porous structure of titanium or a titanium alloy. According to the invention, the porous structure is bonded to the substrate by interlayer disposed intermediate the substrate and the porous structure. The interlayer comprises a cobalt-based alloy including nickel. In one aspect of this form of the invention, a layer of commercially pure titanium may be disposed intermediate the porous structure and the interlayer.

The invention further provides, in one form thereof, a method of manufacturing an orthopaedic implant device having a porous surface. A substrate of a cobalt-based alloy in the form of an orthopaedic implant device is first provided. An interlayer of a cobalt-based alloy including nickel is then applied onto the surface of the substrate. Following the application of the interlayer onto the surface of the substrate, a porous structure of titanium or a titanium alloy is bonded to the interlayer. In one aspect of the invention according to this form thereof, the porous structure is bonded to the interlayer by diffusion bonding. A titanium layer may be provided between the porous structure and the interlayer prior to the assembly being diffusion bonded together.

DESCRIPTION OF THE PREFERRED EMBODIMENT

Figure 1:
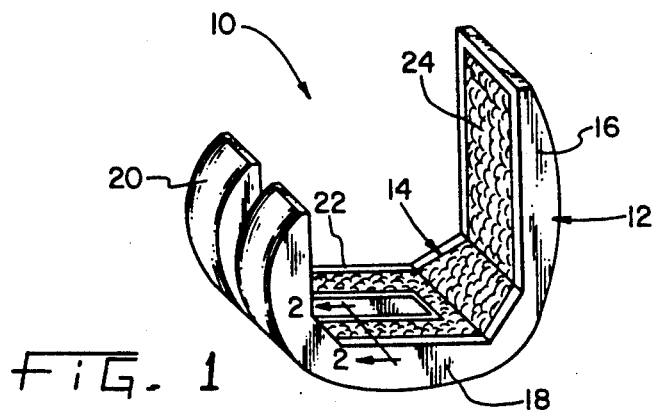
FIG. 1 is a perspective view of the femoral component of a knee prosthesis, representing an orthopaedic implant device that is fabricated from a cobalt-based alloy and includes a titanium porous surface, of the type to which the bonding process of the present invention is applicable.

Referring now to FIG. 1, there is shown an orthopedic implant device 10, i.e., a femoral component of a knee prosthesis, including a substrate 12 of a cobalt-based alloy to which a titanium porous surface structure 14 is bonded in accordance with the present invention. In the disclosed embodiment, device 10 is the femoral component of a knee prosthesis and generally comprises a forward shield portion 16, a lower articulating bearing portion 18, and a pair of rearward, upwardly extending condyles 20, all of which define an inwardly facing surface 22 that contacts and attaches to the distal end of the femur (not shown). In accordance with a preferred embodiment of the invention, porous surface structure 14 is a titanium fiber metal pad 24 partially disposed within a recess 26 in surface 22.

Figure 2:
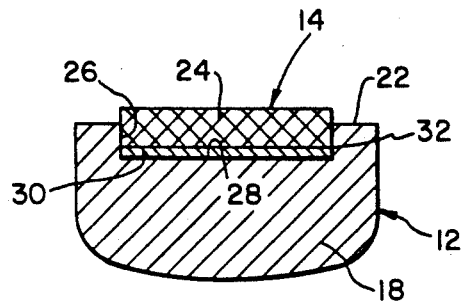
FIG. 2 is a partial sectional view of the knee prosthesis component of FIG. 1, taken along the line 2—2 in FIG. 1 and viewed in the direction of the arrows, in accordance with a one embodiment of the present invention.

Pad 24 is secured to a bottom surface 28 of recess 26 by means of a bonding interlayer 30, as shown in FIG. 2, wherein interlayer 30 comprises a cobalt-based alloy including nickel. As will be more particularly described hereinafter, interlayer 30 is initially applied to surface 28, and is then bonded with titanium fiber metal pad 24 along an interface 32. At interface 32, the nickel in cobalt-based alloy interlayer 30 forms a new alloy with the titanium of pad 24 at bonding temperatures, thereby producing improved corrosion resistance properties as compared to direct bonding of the titanium pad with the cobalt-based alloy substrate.

Figure 3:
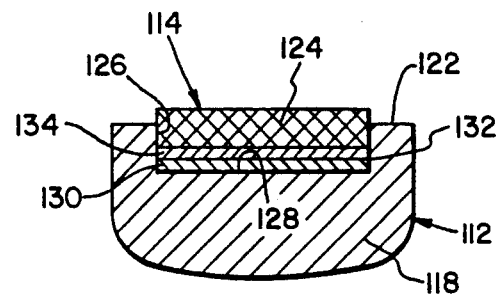
FIG. 3 is a partial sectional view, similar to the view of FIG. 2, of a knee prothesis component in accordance with an alternative embodiment of the invention, wherein the reference numerals used are each 100 greater than those used to describe like features in FIG. 2.

FIG. 3 illustrates an alternative embodiment of the present invention, wherein a layer 134 of commercially pure titanium (CP-titanium) is disposed between interlayer 130 and fiber metal pad 124. According to this embodiment, not only is there a corrosion resistive interface 132 established between titanium layer 134 and interlayer 130, but the bonding strength between pad 124 and interlayer 130 is also enhanced.

A method of bonding titanium porous surface structure 14 to cobalt-based alloy substrate 12 will now be described with reference FIG. 4, wherein an exemplary embodiment of the method of the present invention is diagrammatically illustrated. Generally, block 40 represents the first step of providing an orthopaedic implant device, or component part thereof, that is fabricated from a cobalt-based alloy, i.e., a cobalt-based alloy substrate. In the preferred embodiment, a cast alloy containing cobalt, chromium, and molybdenum is used, having the ASTM designation F75. One such commercial alloy of this designation is ZIMALOY® cobalt-chromium-molybdenum alloy, manufactured by Zimmer, Inc. of Warsaw, Ind., the assignee of the present invention. The cast substrate provided in the first step of the method is preferably cleaned by shot-blasting with stainless steel shot, and by mass tumbling.

Figure 4:
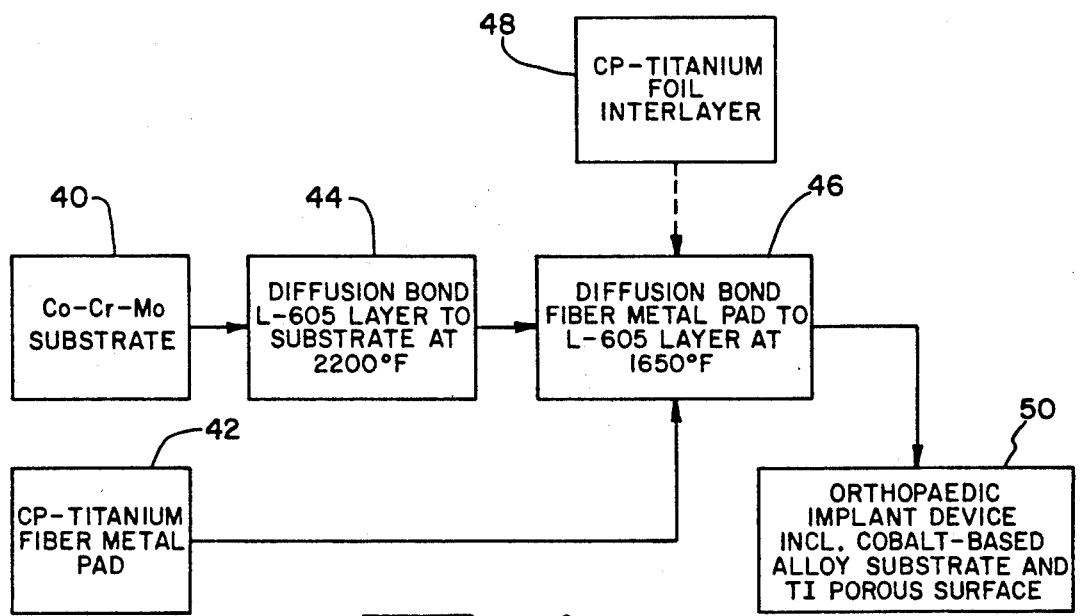
FIG. 4 is a diagrammatic representation of the process steps involved in the bonding method of the present invention.

Block 44 of FIG. 4 represents the next step of the process, during which a layer of a cobalt-based alloy containing nickel is applied to the surface of the substrate. According to the preferred embodiment, the applied layer is L-605 alloy, comprising cobalt, chromium, tungsten, and nickel, and having the ASTM designation F90. When using the L-605, the nickel and tungsten in this interlayer 30 forms a new alloy with the titanium of pad 24 at bonding temperatures. More specifically, an L-605 foil having a thickness of 0.005 inch is diffusion bonded to the surface of the substrate. It has been found that a desirable bonding strength is achieved by diffusion bonding at approximately 2200° F. for 8 hours, in a vacuum furnace having a 400 μm partial pressure of argon. A clamping pressure between the foil and substrate is applied by means of a suitable clamping fixture, e.g., a multi-piece bolted clamping fixture.

It will be appreciated that the temperature, cycle time, partial pressure of argon, and clamping pressure in step 44 can be adjusted to vary the resulting bonding strength between the substrate and interlayer. However, optimum strength properties were observed using a dual diffusion bonding cycle (2 hours and 6 hours) at 2200° F. in a 400 μm partial pressure of argon, wherein clamping pressure is applied by a bolted fixture with the bolts tightened to 8-10 inch-pounds of torque. The two hour cycle may be applied, the materials cooled down, and then the six hour cycle applied. The resulting bonding strength, depending on the surface finish and cleanliness, exhibits a range of 10 ksi to 150 ksi.

The next step of the process, represented by block 46 in FIG. 4, involves diffusion bonding a porous structure to the L-605 layer that has been applied to the substrate. The porous structure is in the form of titanium fiber metal pad 24, as provided for and represented in block 42. The term "titanium fiber metal pad" as used herein is intended to encompass both commercially pure titanium (CP-titanium) and other alloys based on titanium. In the preferred embodiment, fiber metal pad 24 is fabricated from CP-titanium, and has an approximate thickness of 0.055 inch. The fiber metal material from which pad 24 is cut to fit within recess 26, is commercially available as fine wires, manufactured by Astro Metallurgical of Wooster, Ohio. An example of such a suitable porous fiber metal structure is disclosed in U.S. Pat. No. 3,906,550 to Rostoker et al., although is not limited thereto.

According to step 46 of FIG. 4, the CP-titanium fiber metal pad is then diffusion bonded to the pre-applied L-605 layer at a bonding temperature of approximately 1650° F. The same cycle time (8 hours), partial pressure of argon (400 μm), and clamping pressure (8-10 inch-pounds of torque for bolted fixture) that were used for bonding the L-605 to the substrate are again used for bonding the pad to the L-605 layer. Likewise, it is recommended that the same dual diffusion bonding cycle (2 hours and 6 hours) be used to achieve optimum bonding strength.

The bonding strength between the titanium fiber metal pad and the L-605 layer can be further increased by introducing an interlayer of CP-titanium therebetween, as represented by the optional process step of block 48 in FIG. 4 and illustrated by the alternative structure of FIG. 3. Specifically, a CP-titanium foil having a thickness of 0.003 inch is placed between the pad and the L-605 layer prior to clamping and diffusion bonding of the pad. The titanium foil and the titanium pad may be bonded to the pre-applied L-605 layer at the same time. This additional layer increases the bonding surface area between the fiber metal pad and the L-605 layer, thereby enhancing bonding strength. Alternatively, a sheet or coating of CP-titanium or titanium alloy may be used.

As represented by block 50 of FIG. 4, the process of the present invention results in an orthopaedic implant device having a cobalt-based alloy substrate and a titanium porous surface that are bonded together in such a way as to exhibit enhanced bonding strength and corrosion resistance properties.

Interlayer 30, as disclosed herein, is an L-605 alloy layer and is applied to the cobalt-based alloy substrate by diffusion bonding. It is contemplated that MP-35N alloy, comprising cobalt, nickel, chromium, and molybdenum and having ASTM designation F562, may be substituted for the L-605 alloy. Instead of diffusion bonding, it is contemplated that L-605 or MP-35N in the form of a foil or a sheet may also be applied to the substrate by sintering, welding, or cladding. Alternatively, a coating of these alloys may be applied by one or more of a variety of methods, including thermal spray coating, vacuum deposition coating, sputtering, and plating.

Thermal spray coating methods for depositing a thin layer of L-605 or MP-35N alloy to the substrate include combustion flame spray, detonation gun, plasma arc, wire arc, high velocity oxygen fuel (HVOF), and low pressure (hypervelocity) plasma arc spray. The latter two methods have shown particularly good results.

High velocity oxygen fuel (HVOF) is a combustion process which provides improved oxidation control and superior coating bond strength when compared to standard combustion flame processes. The coating alloy powder is introduced into the high speed and temperature combustion gas stream which carries it to the substrate face, where the alloy impacts and bonds. Oxide formation is controlled by using a "rich" fuel mixture, This makes extra fuel available to combine with the free oxygen surrounding the substrate being coated, thereby reducing the amount of oxygen available to form oxides. In addition, the coating particles are bonded to the substrate with a great deal more energy than is available with standard flame spray. Particle velocities approach 2500 feet per second as opposed to 400 feet per second in a typical flame spray. This greatly improves coating bond strength, and when combined with the oxide reduction, greatly reduces coating porosity. Several HVOF processes are commercially available, one in particular being JETCOAT® by Deloro Stellite, of Goshen, Ind.

Low pressure plasma arc spray (LPPS), unlike HVOF, is not a combustion process, but rather uses an electric arc to heat a plasma carrier gas to high temperatures. As in the HVOF process, coating alloy powder is introduced into the high temperature and speed carrier stream. The coating takes place in an inert atmosphere at pressures greatly reduced below atmospheric and approaching a vacuum at 15-60 Torr. The inert atmosphere eliminates oxide formation and allows highly reactive metals, such as titanium, to be deposited without oxide contamination of the coating. The greatly reduced pressure allows the coating particles to reach speeds in excess of 3000 feet per second. The near vacuum inert atmosphere used in this process results in an extremely dense coating with no oxide formation.

Thus, an alternative embodiment of this device is to use the previously described HVOF process to deposit an L-605 or MP-35N corrosion inhibiting interlayer. Alternatively, the low pressure plasma spray (LPPS) process may be used to deposit both an L-605 or MP-35N interlayer and a commercially pure titanium coating on top of the interlayer to enhance bonding between the interlayer and the titanium fiber metal.

In accordance with the ASTM designation F90 referred to above, the chemical requirement for the L-605 alloy are as follows:

| Element | Composition, % Minimum | Maximum |
| --- | --- | --- |
| Carbon | 0.05 | 0.15 |
| Manganese | 1.00 | 2.00 |
| Silicon | — | 0.40 |
| Phosphorus | — | 0.040 |
| Sulfur | — | 0.030 |
| Chromium | 19.00 | 21.00 |
| Nickel | 9.00 | 11.00 |
| Tungsten | 14.00 | 16.00 |
| Iron | — | 3.00 |
| Cobalt* | Balance | Balance |

*Approximately equal to the difference between 100% and the sum percentage of the other specified elements.

In accordance with the ASTM designation F562 referred to above, the chemical requirement for the MP-35N alloy are as follows:

| Element | Composition, % Minimum | Maximum |
| --- | --- | --- |
| Carbon | — | 0.025 |
| Manganese | — | 0.15 |
| Silicon | — | 0.15 |
| Phosphorus | — | 0.015 |
| Sulfur | — | 0.010 |
| Chromium | 19.0 | 21.0 |
| Nickel | 33.0 | 37.0 |
| Molybdenum | 9.0 | 10.5 |
| Iron | — | 1.0 |
| Titanium | — | 1.0 |
| Cobalt* | Balance | Balance |

*Approximately equal to the difference between 100% and the sum percentage of the other specified elements.

These chemical requirements for these two alloys are identified in the indicated ASTM standard.

While the present invention has been illustrated with specific reference to a femoral component of a knee prosthesis, the present invention is equally applicable to other prosthesis, devices, e.g., hip, ankle, elbow, shoulder, wrist, finger, and toe joints, wherein a titanium porous structure is bonded to a cobalt-based alloy substrate by means of an interlayer comprising a cobalt-based alloy including nickel.

It will be appreciated that the foregoing description of a preferred embodiment of the invention is presented by way of illustration only and not by way of any limitation, and that various alternatives and modifications may be made to the illustrated embodiment without departing from the spirit and scope of the invention.

What is claimed is:

1. An orthopaedic implant device having enhanced corrosion resistance properties, comprising:
a substrate of a cobalt-based alloy;
a porous structure of titanium or a titanium alloy; and
an interlayer, intermediate said substrate and said porous structure, comprising a cobalt-based alloy including nickel in an effective amount to enhance bonding strength and corrosion resistance.

2. The orthopaedic implant device of claim 1, and further comprising a layer of commercially pure titanium between said porous structure and said interlayer.

3. The orthopaedic implant device of claim 1 in which said porous structure comprises a fiber metal pad.

4. The orthopaedic implant device of claim 1 in which said interlayer having been formed by initial application to the surface of said substrate and then subsequent diffusion bonding to said porous structure.

5. The orthopaedic implant device of claim 1 in which said substrate comprises a cobalt-based alloy including cobalt and chromium, and said interlayer comprises an alloy including cobalt, chromium, and nickel.

6. The orthopaedic implant device of claim 5 in which said interlayer comprises an alloy including cobalt, chromium, nickel, and tungsten.

7. The orthopaedic implant device of claim 5 in which said interlayer comprises an alloy including cobalt, chromium, nickel, and molybdenum.

8. The orthopaedic implant device of claim 5 in which said porous structure comprises commercially pure titanium.

9. The orthopaedic implant device of claim 5 in which the alloy of said interlayer includes about 9 to 11 percent nickel.

10. The orthopaedic implant device of claim 5 in which the alloy of said interlayer includes about 33 to 37 percent nickel.

* * * * *